(12) United States Patent
Himmelsbach et al.

(10) Patent No.: US 6,242,466 B1
(45) Date of Patent: Jun. 5, 2001

(54) SUBSTITUTED PHENYLAMIDINES

(75) Inventors: Frank Himmelsbach, Mittelbiberach; Brian Guth, Warthausen; Hans-Dieter Schubert, Biberach, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/353,208

(22) Filed: Jul. 14, 1999

Related U.S. Application Data
(60) Provisional application No. 60/101,875, filed on Sep. 25, 1998.

(30) Foreign Application Priority Data

Jul. 23, 1998 (DE) ............................................... 198 33 105

(51) Int. Cl.⁷ ........................ A61K 31/445; C07D 211/32
(52) U.S. Cl. ........................ 514/331; 514/318; 514/326; 514/328; 546/194; 546/209; 546/210; 546/220; 546/221; 546/231; 546/233
(58) Field of Search .................................. 514/318, 326, 514/328, 331; 546/194, 209, 210, 220, 221, 231, 233

(56) References Cited

U.S. PATENT DOCUMENTS
5,958,952 * 9/1999 Himmelsbach et al. ............. 514/327

FOREIGN PATENT DOCUMENTS
0 805 149    11/1997  (EP).
96 33970     10/1996  (WO).

OTHER PUBLICATIONS
Weller, Thomas et al, Orally Active Fibrinogen Receptor Antagonists 2. Amidoximes as Prodrugs of Amidines, J. Med. Chem., 1996, 3139–3147, vol. 39.

Gante, Joachim, et al, New Antithrombotic RGD–Mimetics with High Bioavailability, Bioorganic & Medicinal Chemistry Letters, 1996, 2425–2430, vol. 6, No. 20.

Bundgaard "Design of prodrugs" Elsevier, p. 27–33, 1983.*

Shahrokh et al. "Stability of alkoxycarbonylamidine prodrugs" CA 129:8506, 1998.*

* cited by examiner

*Primary Examiner*—Ceila Chang
(74) *Attorney, Agent, or Firm*—R. P. Raymond; T. X. Witkowski; A. R. Stempel

(57) ABSTRACT

Phenylamidines of the formula (I)

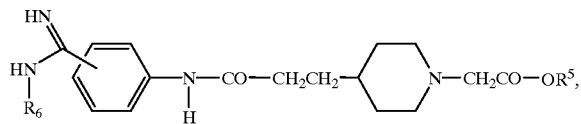

wherein:

$R_6$ is a $C_{5-12}$-alkyloxycarbonyl group, and $R_7$ is a hydrogen atom, or a $C_{1-8}$-alkyl, $C_{4-7}$-cycloalkyl, phenyl-$C_{1-4}$-alkyl, or $R_8$—CO—OCHR$_9$— group, wherein $R_8$ is a $C_{1-4}$-alkyl, $C_{1-4}$-alkoxy, $C_{3-7}$-cycloalkyl, or $C_{4-7}$-cycloalkoxy group, and $R_9$ is a hydrogen atom or a $C_{1-4}$-alkyl group, or a tautomer or pharmaceutically acceptable salt thereof.

These compounds inhibit cell aggregation and are useful for the treatment or prevention of thrombosis, inflammation, bone degradation, tumors and tumor metastasis.

14 Claims, No Drawings

SUBSTITUTED PHENYLAMIDINES

RELATED APPLICATIONS

Benefit of U.S. Provisional Application Ser. No. 60/101,875, filed on Sep. 25, 1998 is hereby claimed.

FIELD OF THE INVENTION

The invention relates to novel substituted phenylamidines, their use as pharmaceutical agents, especially as antithrombotic agents, and methods for their synthesis.

BACKGROUND OF THE INVENTION

WO 96/33970 generically discloses phenylamidines of general formula

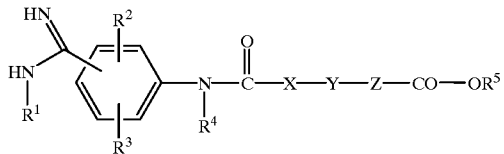

wherein inter alia $R^1$ denotes a $C_{1-4}$-alkyloxycarbonyl group, an aryl-$C_{1-3}$-alkyloxycarbonyl group or a group of formula

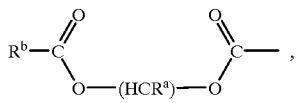

wherein
$R^a$ denotes a hydrogen atom or an alkyl group and $R^b$ denotes an alkyl group or a 3- to 7-membered cycloalkyl group.

DESCRIPTION OF THE INVENTION

It has now been found that the phenylamidines of general formula

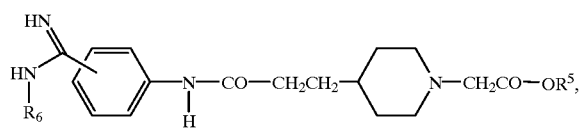

wherein
$R_6$ denotes a $C_{1-18}$-alkyloxycarbonyl or phenyl-$C_{1-4}$-alkyloxycarbonyl group,
$R_7$ denotes a hydrogen atom, a $C_{1-8}$-alkyl, $C_{4-7}$-cycloalkyl, phenyl-$C_{1-4}$-alkyl or $R_8$—CO—OCHR$_9$- group wherein
$R_8$ denotes a $C_{1-4}$-alkyl, $C_{1-4}$-alkoxy, $C_{3-7}$-cycloalkyl or $C_{4-7}$-cycloalkoxy group and
$R_9$ denotes a hydrogen atom or a $C_{1-4}$-alkyl group,
the tautomers, stereoisomers and salts thereof, particularly the physiologically acceptable salts thereof with inorganic or organic acids or bases, have superior pharmacological properties, particularly as antithrombotic agents.

The present invention relates to the compounds of the above general formula I, the tautomers, stereoisomers and salts thereof, particularly the physiologically acceptable salts thereof with inorganic or organic acids or bases, pharmaceutical compositions containing these compounds, their use and processes for preparing them.

Preferred compounds of the above general formula I are those wherein
the substituted amidino group is in the 4 position,
particularly those compounds wherein
$R_6$ denotes a $C_{1-18}$-alkyloxycarbonyl or phenyl-$C_{1-4}$-alkyloxycarbonyl group and
$R_7$ denotes a hydrogen atom, a $C_{1-8}$-alkyl, $C_{5-7}$-cycloalkyl or phenyl-$C_{1-4}$-alkyl group,
the tautomers, stereoisomers and salts thereof.

Particularly preferred compounds of the above general formula I are those wherein
$R_6$ denotes a $C_{1-12}$-alkyloxycarbonyl or phenyl-$C_{1-2}$-alkyloxycarbonyl group and
$R_7$ denotes a $C_{1-8}$-alkyl or $C_{5-7}$-cycloalkyl group,
the tautomers, stereoisomers and salts thereof.

Most particularly preferred compounds of the above general formula I are those wherein
$R_6$ denotes a $C_{5-12}$-akloxycarbonyl or benzyloxycarbonyl group and
$R_7$ denotes a $C_{1-4}$-alkyl or $C_{5-6}$-cycloalkyl group,
the tautomers, stereoisomers and salts thereof.

The following are mentioned as examples of particularly preferred compounds:
(1) 4-[2-[[4-(octyloxycarbonylamidino)phenyl]aminocarbonyl]-ethyl]-1-[(ethoxycarbonyl)methyl]-piperidine,
(2) 4-[2-[[4-(hexyloxycarbonylamidino)phenyl]aminocarbonyl]-ethyl]-1-[(ethoxycarbonyl)methyl]-piperidine,
(3) 4-[2-[[4-(hexyloxycarbonylamidino)phenyl]aminocarbonyl]-ethyl]-1-[(methoxycarbonyl)methyl]-piperidine and
(4) 4-[2-[[4-(octyloxycarbonylamidino)phenyl]aminocarbonyl]-ethyl]-1-[(methoxycarbonyl)methyl]-piperidine
and the salts thereof.

According to the invention the new compounds of general formula I are obtained, for example, by the following method:

reacting a compound of general formula

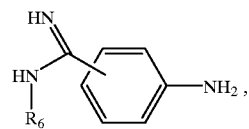

wherein
$R_6$ is as hereinbefore defined, with a compound of general formula

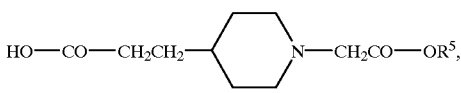

wherein
$R_7$ is as hereinbefore defined, or a reactive derivative thereof and
optionally subsequently converting the group $R_7$ into a hydrogen atom.

Examples of reactive derivatives of a compound of general formula III include the acid chlorides, acid azides, mixed anhydrides with aliphatic or aromatic carboxylic acids or monocarbonates, imidazolides and esters thereof such as the alkyl, aryl and aralkyl esters, e.g. the methyl, ethyl, isopropyl, pentyl, phenyl, nitrophenyl or benzyl esters.

The reaction is expediently carried out in a solvent or mixture of solvents such as methylene chloride, dimethylformamide, dimethylsulphoxide, benzene, toluene, chlorobenzene, tetrahydrofuran, pyridine, pyridine/methylene chloride, pyridine/dimethylformamide, benzene/tetrahydrofuran or dioxane, optionally in the presence of a dehydrating agent, e.g. in the presence of isobutyl chloroformate, thionyl chloride, trimethylchlorosilane, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide, 2-(1H-benzotriazolyl)-1,1,3,3-tetramethyl-uronium salts, N,N'-carbonyldiimidazole, N,N'-thionyldiimidazole, 2-chloro-1-methylpyridinium iodide or triphenylphosphine/carbon tetrachloride, optionally in the presence of dimethylaminopyridine or 1-hydroxy-benzotriazole and/or a base such as triethylamine, N-ethyl-diisopropylamine, pyridine or N-methyl-morpholine, expediently at temperatures between $-10$ and $180°$ C., preferably at temperatures between 0 and $120°$ C.

The subsequent conversion of the group $R_7$ into a hydrogen atom is expediently carried out either in the presence of an acid such as hydrochloric acid, sulphuric acid, phosphoric acid, acetic acid, trichloroacetic acid, trifluoroacetic acid or mixtures thereof or in the presence of a base such as lithium hydroxide, sodium hydroxide or potassium hydroxide in a suitable solvent such as water, water/methanol, water/ethanol, water/isopropanol, methanol, ethanol, water/tetrahydrofuran or water/dioxane at temperatures between $-10$ and $120°$ C., e.g. at temperatures between ambient temperature and the boiling temperature of the reaction mixture.

Moreover, the compounds of general formula I obtained may optionally be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example $(+)$ or $(-)$-menthol and an optically active acyl group in amides, for example, may be a $(+)$- or $(-)$-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds used as starting materials are known from the literature in some cases or may be obtained by methods known from the literature (cf. the Examples).

As already mentioned, the new phenylamidines of general formula I and the salts thereof, particularly the physiologically acceptable salts thereof with inorganic or organic acids or bases, have valuable properties. Thus, when administered orally, the new compounds of general formula I produce high and long-lasting plasma levels compared with the aggregation-inhibiting compound 4-[2-[(4-amidinophenyl)aminocarbonyl]ethyl]-1-carboxymethyl-piperidine (compound A) described in WO 96/33970. Thus, the new phenylamidines of general formula I and the salts thereof have valuable pharmacological properties, not only an anti-inflammatory effect and an inhibitory effect on bone degradation but particularly antithrombotic, antiaggregatory and tumour- or metastasis-inhibiting effects.

For example, the plasma concentration of compound A after oral administration of the compounds of Examples 1 (compound B) and 1(1) (compound C) of the present invention was measured and compared with the plasma concentration of compound A after oral administration of compound A.

After the oral administration of 1 mg/kg of the test compounds to Rhesus monkeys, the concentration of compound A in the plasma was measured 4, 8, 12 and 24 hours after the administration of the substance. To do this the Rhesus plasma was incubated with a suspension of human thrombocytes in plasma and $^3$H-BIBU 52 (cf. DE-A-4,214, 245) as ligand. The free and bound ligand is separated by centrifuging and quantitatively determined by scintillation counting. The concentration of compound A is calculated from the quantity of bound ligand using a calibration curve.

For this purpose donor blood is taken from an anticubital vein and anticoagulated with trisodium citrate (final concentration: 13 mmol/l). The blood is centrifuged for 10 minutes at 170×g and the supunatant platelet-rich plasma (PRP) is removed. The residual blood is sharply centrifuged off again at 3200×g and the supernatant platelet-poor plasma (PPP) is removed.

For the calibration curve for calculating the concentration, 5 $\mu$l of a solution of compound A is added to 995 $\mu$l PPP (final concentration 5000 nmol/l). Further samples of this plasma are diluted with PPP to a final concentration of 2.5 nmol/l.

To 150 μl of plasma sample from Rhesus monkeys or calibration curve plasma are added 10 μl of $^3$H-BIBU 52 (final concentration 10 nmol/l), 10 μl of $^{14}$C-sucrose (370 Bq) and 80 μl of PRP and the mixture is incubated at ambient temperature for 20 minutes. Then the samples are centrifuged at 2000×g for 5 minutes and the supernatant is removed. 100 μl of the supernatant are mixed with 100 μl of NaOH 0.2 mol/l, 15 μl of HCl 5 mol/l and 2 ml of scintillator and the 3H and $^{14}$C radioactivity is measured quantitatively. The pellet is dissolved in 200 μl of NaOH 0.2 mol/l. 180 μl thereof are mixed with 15 μl of HCl 5 mol/l and 2 ml of scintillator and the $^3$H and $^{14}$C radioactivity is measured. The residual plasma remaining in the pellet is determined from the $^{14}$C content and removed. The quantity of bound ligand is determined from the 3H content. The quantity of bound ligand is plotted against the concentration of the calibration curve plasma. The concentration of compound A in the Rhesus plasma is calculated from the quantity of bound ligand in the relevant plasma sample compared with the calibration curve.

The following Table contains the results:

| Substance | conc. of A in [nM], 4h | conc. of A in [nM], 8h | conc. of A in [nM], 12h | conc. of A in [nM], 24h |
|---|---|---|---|---|
| A | 174 | 38 | 25 | 3 |
| B | 133 | 127 | 81 | 51 |
| C | 170 | 123 | 80 | 52 |

In view of their biological properties the new compounds of general formula I according to the invention and their physiologically acceptable salts are suitable for fighting or preventing diseases in which larger or smaller cell aggregations occur or in which cell-matrix interactions are involved, e.g. in combating or preventing venous and arterial thromboses, cerebrovascular diseases, pulmonary embolisms, cardiac infarct, arteriosclerosis, osteoporosis and tumour metasasis and for treating genetically caused or acquired disorders of cell interactions with one another or with solid structures. Moreover, they are suitable for parallel therapy in thrombolysis using fibrinolytics or vascular interventions such as transluminal angioplasty or in the treatment of states of shock, psoriasis, diabetes and inflammation.

For fighting or preventing the abovementioned diseases the dosage is between 0.1 μg and 30 mg/kg of body weight, preferably 1 μg to 15 mg/kg of body weight, taken up to 4 times a day. For this, the compounds of formula I prepared according to the invention, optionally in conjunction with other active substances such as thromboxane receptor antagonists and thromboxane synthesis inhibitors or combinations thereof, ADP-receptor antagonists, clopidogrel, ticlopidine, serotonin antagonists, α-receptor antagonists, alkylnitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatan sulphate, activated protein C, vitamin K antagonists, hirudine, inhibitors of thrombin or other activated clotting factors, may be incorporated, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearyl alcohol, carboxymethylcellulose or fatty substances such as hardened fat or suitable mixtures thereof, in conventional galenic preparations such as plain or coated tablets, capsules, powders, suspensions, solutions, sprays or suppositories.

The following Examples are intended to illustrate the invention more fully:

Preparation of the starting compounds:

EXAMPLE I 4-(hexyloxycarbonylamidino)-aniline 5.1 g of 4-(hexyloxycarbonylamidino)-nitrobenzene are hydrogenated in 100 ml of tetrahydrofuran in the presence of 0.5 g of palladium on activated charcoal at ambient temperature under a hydrogen pressure of 50 psi. Then the catalyst is removed by suction filtering and the filtrate is concentrated by evaporation.

Yield: 4.5 g 100% of theory, $R_f$ value: 0.23 (silica gel; cyclohexane/ethyl acetate=1:1)

The following compounds are obtained analogously to Example I:

(1) 4-(octyloxycarbonylamidino)-aniline $R_f$ value: 0.25 (silica gel; cyclohexane/ethyl acetate=1:1)

(2) 4-(methoxycarbonylamidino)-aniline $R_f$ value: 0.35 (silica gel; methylene chloride/methanol 9:1)

(3) 4-(benzyloxycarbonylamidino)-aniline $R_f$ value: 0.35 (silica gel; methylene chloride/methanol/conc. aqueous ammonia 9:1:0.1)

EXAMPLE II 4-(hexyloxycarbonylamidino)-nitrobenzene 2.8 ml of hexyl chloroformate in 80 ml of tetrahydrofuran are added dropwise to 3.5 g of 4-nitrobenzamidine-hydrochloride and 7.2 g of potassium carbonate in a mixture of 350 ml tetrahydrofuran and 70 ml water, whilst cooling with ice. After 1 hour's stirring in an ice bath the mixture is left to stand overnight at ambient temperature. The organic phase is separated off, washed twice with saturated saline solution, dried and concentrated by evaporation.

Yield: 5.1 g (100% of theory), $R_f$ value: 0.72 (silica gel; cyclohexane/ethyl acetate=1:1)

The following compounds are obtained analogously to Example II:

(1) 4-(octyloxycarbonylamidino)-nitrobenzene mass spectrum: M$^+$=321

(2) 4-(methoxycarbonylamidino)-nitrobenzene melting point: 183–185° C.

(3) 4-(benzloxycarbonylamidino)-nitrobenzene $R_f$ value: 0.88 (silica gel; methylene chloride/methanol/conc. aqueous ammonia=9:1:0.1)

EXAMPLE III

4-[2-(chlorocarbonyl)ethyl]-1-[(ethoxycarbonyl)methyl]-piperidine-hydrochloride

To 1.46 g of 4-(2-carboxyethyl)-1-[(ethoxycarbonyl) methyl]-piperidine in 10 ml of methylene chloride is added 1 ml of saturated ethereal hydrochloric acid. 1.2 g of thionyl chloride are added and the mixture is stirred for 3 hours at ambient temperature. The reaction mixture is concentrated by evaporation and the residue is mixed twice with toluene and again concentrated by evaporation. The crude product is reacted further in Example 1 without purification.

The following compounds are obtained analogously to Example III:

(1) 1-[2-(chlorocarbonyl)ethyl]-4-[(methoxycarbonyl)-methyl]-piperidine-hydrochloride
(2) 4-[2-(chlorocarbonyl)ethyl]-1-[(cyclohexyloxycarbonyl)-methyl]-piperidine-hydrochloride
(3) 4-[2-(chlorocarbonyl)ethyl]-1-[(isopropoxycarbonyl)-methyl]-piperidine-hydrochloride

EXAMPLE IV

4-[2-(carboxy)ethyl]-1-[(ethoxycarbonyl)methyl]-piperidine 10 g of 4-[2-(benzyloxycarbonyl)ethyl]-1-[(ethoxycarbonyl)methyl]-piperidine are hydrogenated in 150 ml of tetrahydrofuran for 4 hours at ambient temperature under a hydrogen pressure of 50 psi in the presence of 1.3 g of palladium on activated charcoal. The reaction mixture is concentrated by evaporation and crystallised with diethylether and a little acetone.

Yield. 5.8 g of (79% of theory),
melting point: 65–67° C.

The following compounds are obtained analogously to Example IV:
(1) 4-(2-carboxyethyl)-1-[(cyclohexyloxycarbonyl)methyl]-piperidine
   melting point: 85–88° C.
(2) 4-(2-carboxyethyl-1-[(isopropoxycarbonyl)methyl]-piperidine
   $R_f$ value: 0.41 (Reversed Phase silica gel; methanol/5% saline=6:4)
(3) 4-(2-carboxyethyl)-1-[(methoxycarbonyl)methyl]-piperidine
   melting point: 82–83° C.

EXAMPLE V

4-[2-(benzyloxycarbonyl)ethyl]-1-[(ethoxycarbonyl)methyl]-piperidine 6.35 g of ethyl bromoacetate in 20 ml of acetonitrile are added dropwise, with stirring, to 9.0 g of 4-[2-(benzyloxycarbonyl)ethyl]-piperidine and 5.2 g of N-ethyldiisopropylamine in 70 ml of acetonitrile, in an ice bath, and the mixture is stirred for 18 hours at ambient temperature. The reaction mixture is concentrated by evaporation and the residue is quickly distributed between tert-butylmethyl ether, ice water and 10 ml of 2N sodium hydroxide solution. The organic phase is separated off, washed with ice water and saturated saline, dried and concentrated by evaporation.

Yield: 10.05 g of (83% of theory),
$R_f$ value: 0.84 (silica gel; methylene chloride/methanol/conc. aqueous ammonia=95:5:1)

The following compounds are obtained analogously to Example V:
(1) 4-[2-(benzyloxycarbonyl)ethyl]-1-[(cyclohexyloxycarbonyl)-methyl]-piperidine
   $R_f$ value: 0.47 (silica gel; methylene chloride/methanol/conc. aqueous ammonia=98:2:0.5).
(2) 4-[2-(benzyloxycarbonyl)ethyl]-1-[(isopropoxycarbonyl)-methyl]-piperidine
   mass spectrum: M⁺=347
(3) 4-[2-(benzyloxycarbonyl)ethyl]-1-[(methoxycarbonyl)-methyl]-piperidine
   $R_f$ value: 0.40 (silica gel; methylene chloride/methanol/conc. aqueous ammonia=9:1:0.1)

EXAMPLE VI

4-[2-(benzyloxycarbonyl)ethyl]-piperidine 9.7 g of 4-(2-carboxyethyl)piperidine-hydrochloride (melting point: 240–250° C., prepared by hydrogenating 3-(4-pyridyl)acrylic acid in glacial acetic acid in the presence of platinum oxide and subsequently treating with hydrochloric acid), 30 ml of benzyl alcohol, 3 g of p-toluenesulphonic acid and 50 ml of toluene are heated for 75 minutes using a water separator. The reaction mixture is concentrated by evaporation in vacuo, the residue is mixed with 50 ml of ice water and extracted three times with tert.butylmethyl ether. The aqueous phase is made alkaline and extracted with tert.butylmethyl ether. The extract is washed with saline, dried and concentrated by evaporation.

Yield: 9.0 g of (73% of theory),
$R_f$ value: 0.18 (silica gel; methylene chloride/methanol/conc. aqueous ammonia=95:5:1)

Preparation of the end compounds:

EXAMPLE 1

4-[2-[[4-(octyloxycarbonylamidinophenyl]-aminocarbonyl]ethyl]-1-[(ethoxycarbonyl)methyl]-piperidine 5.7 g of 4-[2-(chlorocarbonyl)ethyl]-1-[(ethoxycarbonyl)methyl-piperidine-hydrochloride in 30 ml of methylene chloride are added dropwise, within 30 minutes, to 5.1 g of 4-(octyloxycarbonylamidino)aniline and 100 mg of 4-dimethylaminopyridine in 30 ml of pyridine whilst cooling with ice. After standing overnight at ambient temperature the reaction mixture is concentrated by evaporation and the residue is purified by chromatography over a silica gel column with methylene chloride/methanol/conc. aqueous ammonia (9:1:0.1).

Yield: 2.9 g (32% of theory),
melting point: 151–153° C.
mass spectrum: (M+H)⁺=517

The following compounds are obtained analogously to Example 1:
(1) 4-[2-[[4-(hexyloxycarbonylamidino)phenyl]-aminocarbonyl]-ethyl]-1-[(ethoxycarbonyl)methyl]-piperidine
   melting point: 151–153° C.
   mass spectrum: M⁺=489
(2) 4-[2-[[4-(hexyloxycarbonylamidino)phenyl)-aminocarbonyl]-ethyl]-1-[(isopropoxycarbonyl)methyl]-piperidine
   melting point: 161–162° C.
   $R_f$ value: 0.20 (silica gel; methylene chloride/methanol/conc. aqueous ammonia=9:1:0.1)
(3) 4-[2-[[4-(octyloxycarbonylamidino)phenyl]-aminocarbonyl]-ethyl]-1-[(isopropoxycarbonyl)methyl]-piperidine
   melting point: 151–152° C.
   mass spectrum: M⁺=531
(4) 4-[2-[[4-(hexyloxycarbonylamidino)phenyl]-aminocarbonyl]-ethyl]-1-[(cyclohexyloxycarbonyl)methyl]-piperidine
   melting point: 149–151° C.
   mass spectrum: (M+H)⁺=543
(5) 4-[2-[[4-(octyloxycarbonylamidino)phenyl]-aminocarbonyl]-ethyl]-1-[(cyclohexyloxycarbonyl)methyl]-piperidine
   melting point: 157–162° C.
   mass spectrum: (M+H)⁺=571

(6) 4-[2-[[4-(hexyloxycarbonylamidino)phenyl]-aminocarbonyl]-ethyl]-1-[(methoxycarbonyl)methyl]-piperidine melting point: 153–155° C.

$R_f$ value: 0.32 (silica gel; methylene chloride/methanol/conc. aqueous ammonia=9:1:0.1)

(7) 4-[2-[[4-(octyloxycarbonylamidino)phenyl]-aminocarbonyl]-ethyl]-1-[(methoxycarbonyl)methyl]-piperidine melting point: 149–150° C.

mass spectrum: $(M+H)^+=503$ (8) 4-[2-[[4-(methoxycarbonylamidino)phenyl]-aminocarbonyl]-ethyl]-1-[(ethoxycarbonyl)methyl]-piperidine melting point: 175–177° C.

mass spectrum: $(M+H)^+=419$ (9) 4-[2-[[4-(benzyloxycarbonylamidino)phenyl]-aminocarbonyl]-ethyl]-1-[(methoxycarbonyl)methyl]-piperidine melting point: 150–152° C.

Instead of the carboxylic acid chloride the corresponding carboxylic acid is used in the presence of N-methylmorpholine and 2-chloro-1-methylpyridinium iodide in dimethylformamide.

(10) 4-[2-[[4-(decyloxycarbonylamidino)phenyl]-aminocarbonyl]-ethyl]-1-[(ethoxycarbonyl)methyl]-piperidine

(11) 4-[2-[[4-(dodecyloxycarbonylamidino)phenyl]aminocarbonyl]-ethyl]-1-[(ethoxycarbonyl)methyl]-piperidine

(12) 4-[2-[[4-(tetradecyloxycarbonylamidino)phenyl]-aminocarbonyl]-ethyl]-1-[(ethoxycarbonyl)methyl]-piperidine

(13) 4-[2-[[4-(hexadecyloxycarbonylamidino)phenyl]-aminocarbonyl]-ethyl]-1-[(ethoxycarbonyl)methyl]-piperidine

(14) 4-[2-[[4-(octadecyloxycarbonylamidino)phenyl]-aminocarbonyl]-ethyl]-1-[(ethoxycarbonyl)methyl]-piperidine

EXAMPLE 2

4-[2-[[4-(hexyloxycarbonylamidino)phenyl]aminocarbonyl]-ethyl]-1-[(ethoxycarbonyl)methyl]-piperidine methanesulphonate 1,228 ml of a 1-molar solution of methanesulphonic acid in acetone are added dropwise to 600 mg of 4-[2-[[4-hexyloxycarbonylamidino)phenyl]aminocarbonyl]-ethyl]-1-[(ethoxycarbonyl)methyl]-piperidine in 30 ml of acetone. After standing overnight and triturating with a glass rod a solid is obtained which is suction filtered and washed twice with acetone. The solid is then dried in vacuo at 40° C.

Yield: 560 mg (78% of theory), melting point: 117–120° C.

Calc.: C 55.46 H 7.58 N 9.58 S 5.48

Found: 55.56 7.85 9.72 5.54

The following compound is obtained analogously to Example 2:

(1) 4-[2-[[4-(octyloxycarbonylamidino)phenyl]-aminocarbonyl]ethyl]-1-(ethoxycarbonyl)methyl]-piperidine methanesulphonate melting point: 125–127° C.

Calc.: C 56.84 H 7.90 N 9.14 S 5.23

Found: 56.94 7.88 9.32 5.27

EXAMPLE 3

Tablet containing 50 mg of active substance

Composition:

| Ingredient | Amount |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| Total | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 4

Tablet containing 350 mg of active substance

Preparation:

| Ingredient | Amount |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| Total | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

EXAMPLE 5

Capsules containing 50 mg of active substance

Composition:

| Ingredient | Amount |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| Total | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 6

Capsules containing 350 mg of active substance
Composition:

| Ingredient | Amount |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| Total | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

What is claimed is:

1. A compound of the formula (I)

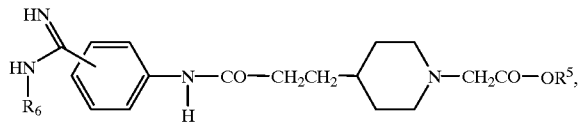

wherein:

$R_6$ is a $C_{5-12}$-alkyloxycarbonyl group, and $R_7$ is a hydrogen atom, or a $C_{1-8}$-alkyl, $C_{4-7}$-cycloalkyl, phenyl-$C_{1-4}$-alkyl, or $R_8$—CO—OCHR$_9$-group, wherein $R_8$ is a $C_{1-4}$-alkyl, $C_{1-4}$-alkoxy, $C_{3-7}$-cycloalkyl, or $C_{4-7}$-cycloalkoxy group, and $R_9$ is a hydrogen atom or a $C_{1-4}$-alkyl group, or a tautomer or pharmaceutically acceptable salt thereof.

2. The compound of formula I according to claim 1, wherein the substituted amidino group is in the 4 position, or a tautomer or pharmaceutically acceptable salt thereof.

3. The compound of formula I according to claim 2, wherein;

$R_7$ is a hydrogen atom, or a $C_{1-8}$-alkyl, $C_{5-7}$-cycloalkyl, or phenyl-$C_{1-4}$-alkyl group, or a tautomer or pharmaceutically acceptable salt thereof.

4. The compound of formula I according to claim 2, wherein:

$R_7$ is a $C_{1-8}$-alkyl or $C_{5-7}$-cycloalkyl group, or a tautomer or pharmaceutically acceptable salt thereof.

5. The compound of formula I according to claim 2, wherein:

$R_7$ is a $C_{1-4}$-alkyl- or $C_{5-6}$-cycloalkyl group, or a tautomer or pharmaceutically acceptable salt thereof.

6. A compound selected from the group consisting of:

(1) 4-[2-[[4-(octyloxycarbonylamidino)phenyl]-aminocarbonyl]ethyl]-1-[(ethoxycarbonyl)methyl]-piperidine, (2) 4-[2-[[4-(hexyloxycarbonylamidino)phenyl]-aminocarbonyl]-ethyl]-1-[(ethoxycarbonyl)methyl]-piperidine, (3) 4-[2-[[4-(hexyloxycarbonylamidino)phenyl]-aminocarbonyl]ethyl]-1-[(methoxycarbonyl)methyl]-piperidine and (4) 4-[2-[[4-(octyloxycarbonylamidino)phenyl]-aminocarbonyl]ethyl]-1-[(methoxycarbonyl)methyl]-piperidine or a phannaceufically acceptable salt thereof.

7. 4-[2-[[4-(Hexyloxycarbonylamidino)phenyl]-aminocarbonyl]-ethyl]-1-[(ethoxycarbonyl)methyl]-piperidine or a pharmaceutically acceptable salt thereof.

8. 4-[2-[[4-(octyloxycarbonylamidino)phenyl]-aminocarbonyl]ethyl]-1-[(ethoxycarbonyl)methyl]-piperidine or a pharmaceutically acceptable thereof.

9. A pharmaceutical comprising a compound in accordance with one of claims 1, 2, 3, 4, 5, 6, 7, or 8.

10. A method for the treatment or prophylaxis of thrombosis which comprises administering to a host in need of such treatment or prophylaxis an antithrombotic amount of a compound in accordance with one of claims 1, 2, 3, 4, 5, 6, 7, or 8.

11. A method for the treatment or prophylaxis of bone degradation which comprises administering to a host in need of such treatment or prophylaxis a bone degradation inhibiting amount of a compound in accordance with one of claims 1, 2, 3, 4, 5, 6, 7, or 8.

12. A method for the treatment of a disease in which larger or smaller cell aggregations occur or which involves cell-matrix interactions, the method comprising administering to a host in need of such treatment a therapeutic amount of a compound in accordance with one of claims 1, 2, 3, 4, 5, 6, 7, or 8.

13. A method for inhibiting the metastasis of a tumor which comprises administering to a host having a tumor a metastasis-inhibiting amount of a compound in accordance with one of claims 1, 2, 3, 4, 5, 6, 7, or 8.

14. A method for the treatment of inflammation which comprises administering to a host having an inflammatory condition an anti-inflammatory amount of a compound in accordance with one of claims 1, 2, 3, 4, 5, 6, 7, or 8.

* * * * *

UNITED STATES PATENT AND TRADEMARK OFFICE
CERTIFICATE OF CORRECTION

PATENT NO. : 6,242,466 B1
DATED : June 5, 2001
INVENTOR(S) : Himmelsbach et al.

It is certified that error appears in the above-identified patent and that said Letters Patent is hereby corrected as shown below:

Abstract,
Formula [I], that portion of the formula reading "-$OR_5$" should read -- $OR_7$ --

Column 1,
Line 49, formula [I], that portion of the formula reading "-$OR_5$" should read -- $OR_7$ --.

Column 2,
Line 59, formula [III], that portion of the formula reading "-$OR_5$" should read -- $OR_7$ --.

Column 11,
Line 27, claim 1, formula [1], that portion of the formula reading "-$OR_5$" should read -- $OR_7$ --.

Column 12, claim 6,
Line 18, "phannacefically" should read -- pharmaceutically --.

Signed and Sealed this

Thirtieth Day of October, 2001

Attest:

NICHOLAS P. GODICI
Attesting Officer   Acting Director of the United States Patent and Trademark Office